(12) United States Patent
Narayanan

(10) Patent No.: US 6,593,148 B1
(45) Date of Patent: Jul. 15, 2003

(54) CYANINE DYE COMPOUNDS AND LABELING METHODS

(75) Inventor: Narasimhachari Narayanan, Lincoln, NE (US)

(73) Assignee: Li-Cor, Inc., Lincoln, NE (US)

( * ) Notice: Subject to any disclaimer, the term of this patent is extended or adjusted under 35 U.S.C. 154(b) by 0 days.

(21) Appl. No.: 09/520,770

(22) Filed: Mar. 7, 2000

Related U.S. Application Data

(63) Continuation-in-part of application No. 09/143,153, filed on Aug. 20, 1998, now abandoned, which is a division of application No. 08/500,691, filed on Jul. 11, 1995, now Pat. No. 6,086,737, which is a continuation-in-part of application No. 08/204,627, filed on Mar. 1, 1994, now Pat. No. 5,571,388.

(51) Int. Cl.[7] .................. G01N 33/533; C07D 209/08; C07K 17/02
(52) U.S. Cl. .................. 436/546; 435/6; 436/546; 436/800; 530/391.3; 530/404; 530/405
(58) Field of Search .................. 548/156, 219, 548/455; 435/6; 530/391.1, 391.3, 404, 405; 436/546, 806

(56) References Cited

U.S. PATENT DOCUMENTS

| | | |
|---|---|---|
| 3,148,187 A | 9/1964 | Heseltine |
| 4,040,825 A | 8/1977 | Steiger et al. |
| 4,138,551 A | 2/1979 | Steiger et al. |
| 4,268,622 A | 5/1981 | Adachi et al. |
| 4,337,063 A | 6/1982 | Mihara et al. |
| 4,414,325 A | 11/1983 | Masuda et al. |
| 4,542,104 A | 9/1985 | Stryer et al. |
| 4,584,277 A | 4/1986 | Ullman |
| 4,748,129 A | 5/1988 | Chang et al. |
| 4,981,977 A | 1/1991 | Southwick et al. |
| 5,445,672 A | 8/1995 | Closs et al. |
| 5,519,145 A * | 5/1996 | Fabricius et al. |
| 5,571,388 A * | 11/1996 | Patonay et al. |
| 5,627,027 A | 5/1997 | Waggoner |
| 6,086,737 A | 7/2000 | Patonay et al. |
| 6,136,612 A | 10/2000 | Della Ciana et al. |
| 6,197,956 B1 | 3/2001 | Randall et al. |
| 6,204,389 B1 | 3/2001 | Randall et al. |

FOREIGN PATENT DOCUMENTS

| | | |
|---|---|---|
| EP | 670374 A1 * | 9/1995 |
| JP | 6-145539 | 5/1994 |
| WO | WO 95/04747 A1 | 2/1995 |
| WO | WO 96/33406 A1 | 10/1996 |
| WO | 98/52609 A1 * | 11/1998 |
| WO | WO 00/16810 A1 | 3/2000 |

OTHER PUBLICATIONS

Narayanan et al., "New NIR Dyes: Synthesis, Spectral Properties and Applications in DNA Analyses," *Near–Infrared Dyes for High Technology Applications*, 1998, 141–158.

Lipowska et al., "New Near–Infrared Cyanine Dyes for Labelling of Proteins," *Synthetic Communications*, 23(21), 3087–3094 (1993).

Flanagan et al., "Functionalized Tricarbocyanine Dyes as Near–Infrared Fluorescent Probes for Biomolecules," *Bioconjugate Chem.*, 1997, 8, 751–756.

Mujumdar et al., "Cyanine Dye Labelling Reagents: Sulfoindocyanine Succinimidyl Esters," *Bioconjugate Chemistry*, Mar./Apr. 1993, vol. 4, No. 2, pp. 105–111.

Narayanan et al., "A New Method for the Synthesis of Heptamethine Cyanine Dyes: Synthesis of New Near–Infrared Fluorescent Labels," *The Journal of Organic Chemistry*, 1995, 60, 2391–2395.

Williams et al., "Comparison of Covalent and Noncovalent Labeling with Near–Infrared Dyes for the High–Performance Liquid Chromatographic Determination of Human Serum Albumin," *Anal. Chem.*, 1993, 65, 601–605.

Strekowski et al., "Substitution Reactions of a Nucleofugal Group in Heptamethine Cyanine Dyes. Synthesis of an Isothiocyanato Derivative for Labeling of Proteins with a Near–Infrared Chromophore," *J. Org. Chem.*, 1992, 57, 4578–4580.

Packard et al., "Intracellular Dye Heterogeneity Determined by Fluorescence Lifetimes," *Biochimica et Biophysica Acta*, 769 (1984) 201–203.

Ficken, "Cyanine Dyes," *The Chemistry of Synthetic Dyes*, vol. IV, Chapter V, 1971, 211–213, 230–231.

Sturmer "Syntheses and Properties of Cyanine and Related Dyes," Chapter VIII, 441–483, 488–553, 582–587, 1977.

* cited by examiner

Primary Examiner—Mary E. Ceperley
(74) Attorney, Agent, or Firm—Rothwell, Figg, Ernst & Manbeck

(57) ABSTRACT

A novel cyanine dye having the formula

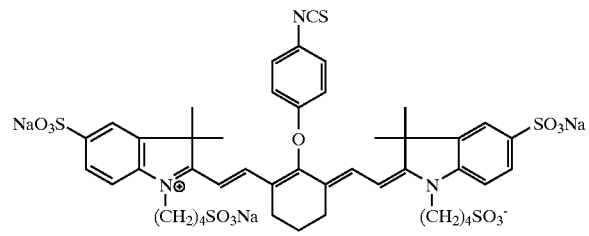

is useful for labeling biological and nonbiological molecules.

2 Claims, 6 Drawing Sheets

CYANINE DYE COMPOUNDS AND LABELING METHODS

REFERENCE TO RELATED APPLICATIONS

This application is a continuation-in-part of U.S. patent application Ser. No. 09/143,153, filed Aug. 20, 1998, now abandoned which is a divisional of U.S. patent application Ser. No. 08/500,691, filed Jul. 11, 1995, U.S. Pat. No. 6,086,737 which is a continuation-in-part of U.S. patent application Ser. No. 03/204,627, filed Mar. 1, 1994, now U.S. Pat. No. 5,571,388.

BACKGROUND OF THE INVENTION

This invention relates to compounds useful for the labeling of biological materials, such as DNA and proteins, and non-biological materials to make the materials fluorescent and easily detectable. In one embodiment, the compounds can be used to label and then sequence DNA after irradiation by light from a laser.

In one class of techniques for sequencing DNA, identical strands of DNA are marked with a fluorescent dye. The strands are marked by attaching specially synthesized fluorescent oligonucleotide primers or probes to the strands of DNA, or by attaching the fluorescent dye directly to the strands. The strands are separated into four aliquots. The strands in a given aliquot are either individually cleaved at or synthesized to any base belonging to only one of the four base types, which are adenine, guanine, cytosine, and thymine (hereinafter A, G, C and T). The adenine-, guanine-, cytosine-, and thymine-terminated strands are then electrophoresed for separation and the separated strands are irradiated by a laser and the emission from the fluorescent dye detected. The rate of electrophoresis indicates the DNA sequence.

Cyanine dyes are known to absorb far-red (600–700 nm) and near-infrared (700–1200 nm) light and techniques for the synthesis of derivatives of the cyanine dyes are known. It has been difficult, however, to obtain chromophores with absorption and emission bands that reduce the effect of background noise during gel electrophoresis when irradiating with a diode laser scanner. Some dyes, not described herein, exhibit absorption in wavelengths greater than 1200 nm (infrared) and also would provide discrimination against background noise.

Suitable types of cyanine dyes include heptamethine cyanine dyes. Cyanine dyes traditionally have been synthesized by a condensation reaction between a heterocyclic base containing an activated methyl group and an unsaturated bisaldehyde or its equivalent, usually a Schiff base in the presence of a catalyst. Sodium acetate has been used most frequently as a catalyst. In addition to ethanol, solvents such as acetic acid and/or acetic anhydride also have been commonly used, as in the synthesis of heptamethine pyrylium dyes.

This procedure suffers from several disadvantages, such as, for example: (1) the purification of the product is very difficult because of the side products due to aniline; (2) the use of a catalyst interferes with the purity of the product and warrants repeated purification; (3) the reaction is generally fast and cannot be employed for the synthesis of nonsymmetric dyes in one pot; and (4) the scaling up of the reaction products to larger gram quantities leads to several additional problems resulting in poor quality and yield.

The present invention describes new cyanine dyes, advantageous methods of making them, and the labeling of various materials with these dyes.

SUMMARY OF THE INVENTION

Accordingly, it is an object of the present invention to provide novel dyes that fluoresce in the far red, near infrared, or infrared region in selected wavelengths when attached to biological and nonbiological materials and that have sufficient quantum yield to make detection feasible.

It is a further object of the invention to provide a method of synthesizing new dyes having these characteristics.

It also is an object of the invention to provide a novel probe or primer containing a dye that fluoresces in the far red, near infrared, or infrared region.

It is a further object of the invention to provide a novel fluorescent marker, method of synthesizing the marker and method of attaching the marker to DNA and other biological and nonbiological material.

It is a further object of the invention to provide a novel technique for DNA sequencing.

In accordance with the present invention, novel cyanine dyes are provided which can be used to label biological molecules, such as DNA, proteins and antibodies, and non-biological molecules. The dyes have preferred spectra and high absorption and fluorescence properties. Each dye has at least one reactive group which enables it to be coupled easily to the molecule of interest.

The dyes of the invention have an absorption band and an emission band within a region encompassing the far red, near infrared, or infrared region when attached to a probe, primer, oligonucleotide or other molecule. The dyes are selected to provide high quantum yield in an optical band selected to reduce background noise. The preferred dyes for many applications calling for the labeling of biomolecules are cyanine dyes which have an NCS group, a carboxyl group or a hydroxy group. The NCS group reacts with the amino group of the biomolecule to form a thiourea linkage. A carboxyl group on the dye can be converted to an NHS ester that reacts with the amino group of the biomolecule to form a stable amide linkage, and a hydroxyl group on the dye can react with a biomolecule to form stable carbamate linkages through NHS carbonate ester activation.

The preferred dyes are heptamethine cyanines which efficiently absorb light having wavelengths in the region of 630 to 900 nm. These wavelengths are suitable for reducing background fluorescence in DNA sequencing and correspond to the radiation wavelengths of diode lasers made of such materials as GaAlAs, GaAs, InGaAlP, GaInP, AlGaAs, AlGaInP, GaAlP, InGaAsP, GaInP/AlInP, InGaP/InGaAlP, or GaInP/AlGaInP. The GaAlAs diode, for example, emits light at wavelengths in the region of 780–800 nm and is used for scanning the gel electrophoresis sandwich used for DNA sequencing.

The sequencing of far red, near infrared, and infrared fluorescent dye-labeled DNA and the detection of the DNA after irradiation by far red, near infrared, or infrared light from a laser diode can be readily accomplished using the novel compounds of this invention. The strands of DNA are continuously electrophoresed and identified for any of several purposes, such as, for example: (1) DNA sequencing and (2) analysis of strands varying in length as prepared by such techniques as restriction enzyme cutting or polymerase chain reaction (PCR).

To aid in identification, the strands are marked with fluorescent labels that emit light in the far red, near infrared, or infrared region. The strands are irradiated with light in the far red, near infrared, or infrared region and the light emitted from the fluorescent labels is detected and used to obtain information about the DNA strands.

The marking is accomplished by direct labeling of fluorescent markers to the strands or by fluorescently labeled probes or primers hybridized to the separated strands. The labeled strands are detected by scanning with a far red, near infrared, or infrared laser diode light source.

SUMMARY OF THE DRAWINGS

The above noted and other features of the invention will be better understood from the following detailed description when considered with reference to the accompanying drawings in which.

DETAILED DESCRIPTION

Figure 1:
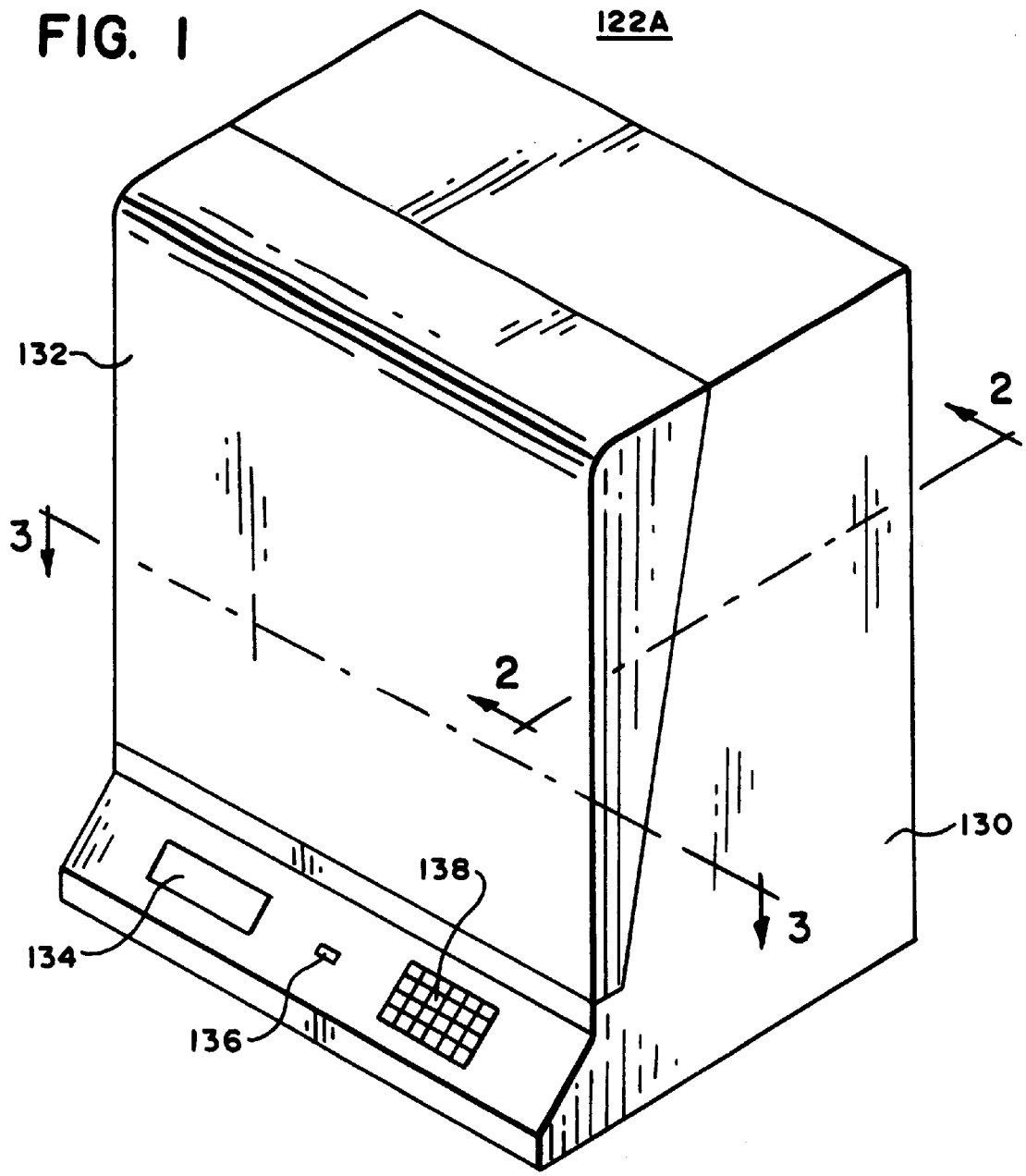
FIG. 1 is a perspective view of an embodiment of a sequencer usable in the invention.

The labeling of biomolecules and nonbiological molecules is accomplished using a far red, near infrared, or infrared label prepared for this purpose as described in detail below. In a preferred embodiment, DNA is labeled and detected after irradiation by far red, infrared or near infrared light from a laser diode and either directly attached to the DNA or attached to probes or primers that will be attached to the DNA. In this specification the word "infrared" will be used at times to include far red wavelengths (600–700 nm), near infrared (700–1200 nm) and infrared (1200–4000 nm). The strands of DNA are continuously electrophoresed and identified for any of several purposes, such as, for example: (1) DNA sequencing and (2) analysis of strands varying in length as prepared by such techniques as restriction enzyme cutting or polymerase chain reaction (PCR).

Molecules of interest are marked with fluorescent labels that have their maximum fluorescence and their maximum absorption at wavelengths of light in the far red, near infrared, or infrared region. The labeled molecules then are irradiated with light in the far red, near infrared, or infrared region from a laser diode and the light emitted from the fluorescent labels is detected and used to obtain information about the labeled molecules. The detector includes a light sensor which is preferably an avalanche photodiode sensitive to the infrared light emission of the marker. It may include a filtering system having a pass band suitable for passing selectively the optimum emission of the fluorescent marker to the light sensor.

To mark the molecule of interest, a dye is prepared having the desired properties of an absorption band and an emission band within a region encompassing the far red, near infrared, or infrared region when attached to a probe, primer, oligonucleotide or other molecule. The dye should provide high quantum yield in an optical band selected to reduce background noise.

For DNA sequencing, preferred dyes are heptamethine cyanine dyes which efficiently absorb light having wavelengths in the region of 750 to 820 nm (nanometers) (maximum absorbance wavelength). Such wavelengths are suitable for reducing background fluorescence in DNA sequencing and corresponds to the radiation wavelength of the GaAlAs diode laser which is 780–800 nm. The GaAlAs diode is used for irradiating the gel electrophoresis sandwich, column, or capillary used for DNA sequencing.

In accordance with the present invention, compounds suitable as dyes have been synthesized and isolated which have the following general formula:

Formula I

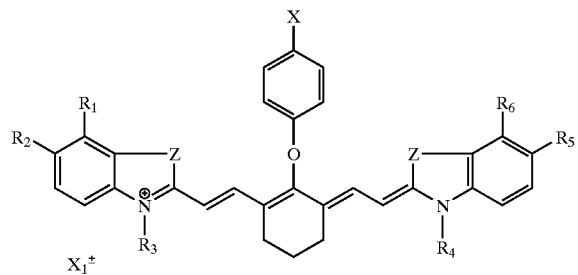

wherein X, $X_1^\pm$, Z, and each of $R_1$–$R_6$ are as defined below.

In a first preferred embodiment within the foregoing general formula:

each Z, independently, is O, S, or $C(CH_3)_2$;

X is H, NCS, $NO_2$, OMe, $N(CH_2COOH)_2$, $(CH_2)_wCH_3$ or $(CH_2)_nX'$;

wherein X' is NCS, OH, phosphoramidite, $NH_2$, COOH, COONHS-ester (COONHSE), or sulfosuccinimidyl ester, n is an integer from 1 to 19 and w is an integer from 0 to 19;

each of $R_1$ and $R_6$ is H;

each of $R_2$ and $R_5$, independently, is H, $OCH_3$ or $SO_3^-$;

each of $R_3$ and $R_4$ is $(CH_2)_rCH_3$, $(CH_2)_mR'$ or $(CH_2)_pSO_3^-$;

wherein R' is NCS, OH, phosphoramidite, $NH_2$, COOH, COONHSE or sulfosuccinimidyl ester, m is an integer from 1 to 20, p is an integer from 2 to 4, and r is an integer from 1 to 19; and $X_1^\pm$ is one or more optionally present counterions having a total charge of from −1 to +3, to maintain overall electrical neutrality of the compound;

provided that both $R_3$ and $R_4$ are not $(CH_2)_mR'$ and that if one of $R_3$ and $R_4$ is $(CH_2)_mR'$, then X is not NCS or $(CH_2)_nX'$ and if X is NCS or $(CH_2)_nX'$, then neither $R_3$ nor $R_4$ is $(CH_2)_mR'$;

and further provided that if $R_3$ and $R_4$ are both $(CH_2)_pSO_3^-$ or $CH_2CH_3$, X is NCS, $(CH_2)_nNCS$ or $(CH_2)_nCOOH$, and Z is $C(CH_3)_2$, both $R_2$ and $R_5$ are not H.

In a second preferred embodiment within the general formula:

$R_1$ and $R_2$ together are a four carbon bridge which together with the carbons to which they are attached form a 6-membered aromatic ring;

each Z, independently, is O, S, or $C(CH_3)_2$;

X is H, NCS, $NO_2$, OMe, $N(CH_2COOH)_2$, $(CH_2)_wCH_3$ or $(CH_2)_nX'$;

wherein X' is NCS, OH, phosphoramidite, $NH_2$, COOH, COONHS-ester (COONHSE), or sulfosuccinimidyl ester, n is an integer from 1 to 19 and w is an integer from 0 to 19;

$R_6$ is H;

$R_5$ is H, $OCH_3$ or $SO_3^-$;

each of $R_3$ and $R_4$ is $(CH_2)_rCH_3$, $(CH_2)_mR'$ or $(CH_2)_pSO_3^-$;

wherein R' is NCS, OH, phosphoramidite, $NH_2$, COOH, COONHSE, or sulfosuccinimidyl ester, m is an integer from 1 to 20, p is an integer from 2 to 4, and r is an integer from 0 to 19; and $X_1^\pm$ is one or more optionally present counterions having a charge of from −1 to +3 to maintain electrical neutrality of the compound;

provided that both $R_3$ and $R_4$ are not $(CH_2)_mR'$ and that if one of $R_3$ and $R_4$ is $(CH_2)_mR'$, then X is not NCS or $(CH_2)_nX'$ and if X is NCS or $(CH_2)_nX'$, then neither $R_3$ nor $R_4$ is $(CH_2)_mR'$, and further provided that if each of X, $R_5$ and $R_6$ is H, each Z is $C(CH_3)_2$, and $R_4$ is $(CH_2)_pSO_3^-$ and $R_3$ is either $(CH_2)_mOH$ or $(CH_2)_m$-phosphoramidite, then m is 3.

In a third preferred embodiment within the foregoing general formula:

$R_1$ and $R_2$ together are a four carbon bridge which together with the carbons to which they are attached form a 6-membered aromatic ring;

$R_5$ and $R_6$ are a four carbon bridge which together with the carbons to which they are attached form a 6-membered aromatic ring;

each Z, independently, is O, S or $C(CH_3)_2$;

X is H, NCS, $NO_2$, OMe, $N(CH_2COOH)_2$, $(CH_2)_wCH_3$ or $(CH_2)_nX'$;

wherein X' is NCS, OH, phosphoramidite, $NH_2$, COOH, COONHS-ester (COONHSE), or sulfosuccinimidyl ester, n is an integer from 1 to 19 and w is an integer from 0 to 19, each of $R_3$ and $R_4$ is $(CH_2)_rCH_3$, $(CH_2)_mR'$ or $(CH_2)_pSO_3^-$;

wherein R' is NCS, OH, phosphoramidite, $NH_2$, COOH, COONHSE, or sulfosuccinimidyl ester, m is an integer from 1 to 20, p is an integer from 2 to 4, and r is an integer from 0 to 19; and $X_1^\pm$ is one or more optionally present counterions having a charge of from −1 to +3 to maintain electrical neutrality of the compound;

provided that both $R_3$ and $R_4$ are not $(CH_2)_mR'$ and that if one of $R_3$ and $R_4$ is $(CH_2)_mR'$, then X is not NCS or $(CH_2)_nX'$ and if X is NCS or $(CH_2)_nX'$, then neither $R_3$ nor $R_4$ is $(CH_2)_mR'$, and further provided that if X is H, each Z is $C(CH_3)_2$, and $R_4$ is $(CH_2)_pSO_3^-$, then $R_3$ is not $(CH_2)_mOH$ or $(CH_2)_m$-phosphoramidite.

In each of the three embodiments set forth above, it is preferred that n is an integer from 1 to 3, that w is an integer from 0 to 6, that m is an integer from 1 to 6; that p is an integer from 2 to 4 and r is an integer from 0 to 6. Often, in more preferred embodiments, w is an integer from 1 to 3, m is an integer from 3 to 6, and r is an integer from 1 to 3. It further is preferred that $X_1^\pm$ comprises a halide, perchlorate or p-toluene sulfonate ion, or an alkali metal ion, such as sodium, potassium or lithium ion.

The present invention also encompasses compounds having the following general formula:

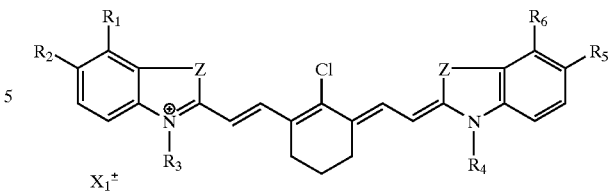

wherein $R_1$ and $R_2$ together form a four carbon bridge which together with the carbons to which they are attached form a 6-membered aromatic ring;

$X_1^\pm$ is one or more optionally present counterions having a total charge of from −1 to +3 to maintain overall electrical neutrality of the compound;

each Z, independently, is O, S or $C(CH_3)_2$;

$R_6$ is H;

$R_5$ is H, $OCH_3$ or $SO_3^-$; and each of $R_3$ and $R_4$, independently, is $(CH_2)_rCH_3$, $(CH_2)_mR'$ or $(CH_2)_pSO_3^-$;

Wherein R' is NCS, OH, phosphoramidite, $NH_2$, COOH, COONHS ester or $(CH_2)_mCOON$-hydroxysulfosuccinimidyl ester, m is an integer from 1 to 20, p is an integer from 2 to 4, and r is an integer from 0 to 19;

provided that both $R_3$ and $R_4$ are not $(CH_2)_mR'$ and that if Z is $C(CH_3)_2$ and one of $R_3$ and $R_4$ is $(CH_2)_pSO_3^-$, the other is not $(CH_2)_mOH$.

These asymmetric chloro dyes are precursors of the dyes of the second preferred embodiment, above.

The compounds of the first, second and third embodiments of the general formula above are useful as labels of biological and nonbiological molecules. Biological molecules include, but are not limited to, natural and synthetic DNA, RNA, PNA (peptide nucleic acids) peptides, proteins, cells, antibodies, antigens, haptens, polysaccharides, oligosaccharides, carbohydrates, avidin, streptavidin, hormones, enzyme substrates, nucleosides, nucleotides and analogs thereof. Preferred biological molecules are DNA and RNA, PNA, oligonucleotides, nucleosides and nucleotides or analogs thereof, such as dideoxynucleotides (terminators). Nonbiological molecules can include, for example, trace compounds, the presence of which in test samples is to be detected.

The heptamethine cyanine dyes of the present invention are derived from benzoxazoles, naphthoxazoles, benzothiazoles, naphthiazoles, indoles and benzindoles. The compounds strongly absorb in the 700 to 850 nm region. All of the dyes of the present invention possess high molar absorbtivity in the 100,000 to 250,000 moles/liter/cm range typical of cyanine dyes and have strong fluorescence with quantum yields in the range of 0.1 to 0.5 depending upon the solvent. The three classes of dyes provide a wide range of wavelength choices suitable for excitation by commercially available lasers.

Each of the three embodiments is discussed in more detail below.

In one preferred set of compounds within embodiment 1, X is NCS, $(CH_2)_nOH$, $(CH_2)_n$phosphoramidite, $(CH_2)_nNCS$, $(CH_2)_nCOOH$, $(CH_2)_nCOONHS$-ester or $(CH_2)_nCOON$-hydroxy sulfosuccinimidyl ester; each of $R_2$ and $R_5$ is hydrogen; and each of $R_3$ and $R_4$ is either $(CH_2)_rCH_3$ or $(CH_2)_pSO_3^-$, wherein n, p and r are as defined above and both of $R_3$ and $R_4$ are not $(CH_2)_pSO_3^-$ if X is $(CH_2)_nCOOH$ or $(CH_2)_nNCS$ and each Z is $C(CH_3)_2$. Especially preferred are compounds wherein n is 1 to 3 and r is 0 to 6 and most preferred compounds are those wherein r is 1 to 3. These cyanine dyes have a high quantu/m yield in methanol of about 35%. When Z is O, the wavelength of absorption and fluorescence range from about 700–740 nm. When Z is S, the dyes absorb and emit in the range of about 790–840 nm, and when Z is $C(CH_3)_2$, the dyes absorb and emit in the range of about 760–810 nm.

Particularly preferred compounds within this group are

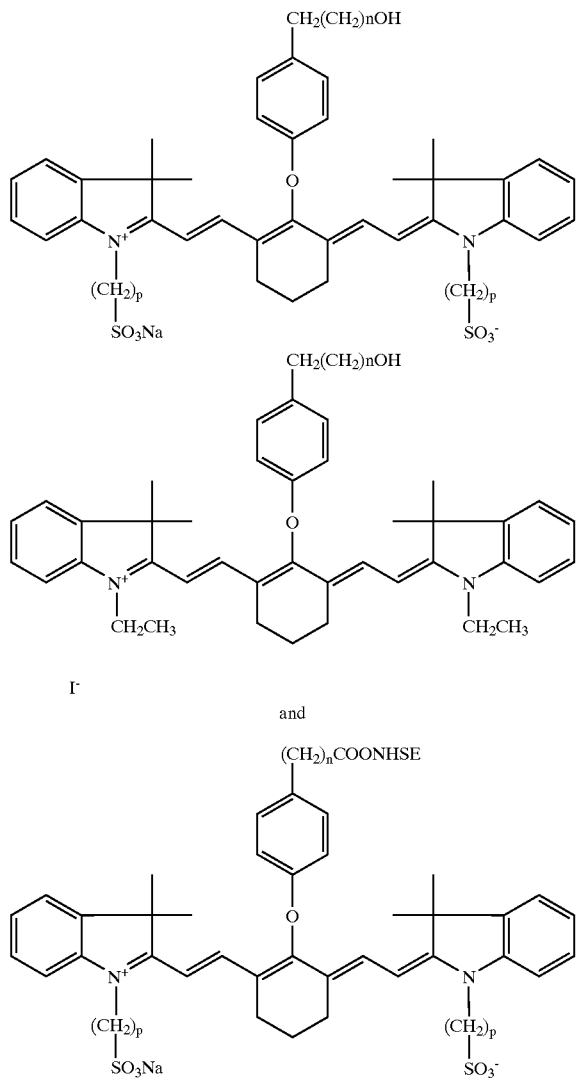

and wherein n is an integer from 1 to 3.

Also preferred are compounds wherein X is NCS, $(CH_2)_n$OH, $(CH_2)_n$phosphoramidite, $(CH_2)_n$NCS, $(CH_2)_n$COOH, $(CH_2)_n$COONHSE or $(CH_2)_n$COON-hydroxy sulfosuccinimidyl ester; at least one of $R_2$ and $R_5$ is $SO_3^-$ or $OCH_3$; and $R_3$ and $R_4$, independently, are selected from $(CH_2)_rCH_3$ and $(CH_2)_pSO_3^-$ and n, r and p are as defined above.

Other particularly preferred compounds within this embodiment are those wherein each of $R_2$ and $R_5$ is $SO_3^-$, each of $R_3$ and $R_4$ is $(CH_2)_pSO_3^-$, and X is selected from NCS, $(CH_2)_n$COOH, $(CH_2)_n$COONHS-ester or $(CH_2)_n$COON-hydroxy sulfosuccinimidyl ester, especially with n being an integer of 1–3. One such preferred set of compounds includes those where each of $R_2$ and $R_5$ is $SO_3^-$, each of $R_3$ and $R_4$ is $(CH_2)_pSO_3^-$ and X is NCS. Also preferred are compounds where each of $R_2$ and $R_5$ is $SO_3^-$, each of $R_3$ and $R_4$ is $CH_2CH_3$, and X is NCS, $(CH_2)_n$COOH, $(CH_2)_n$COONHSE or $(CH_2)_n$COON-hydroxy sulfosuccinimidyl ester, especially wherein n is an integer from 1 to 3. These compounds are preferred because of their aqueous solubility and biocompatibility. When X is NCS, $(CH_2)_n$COOH, $(CH_2)_n$COONHSE or $(CH_2)_n$COON-hydroxy sulfosuccinimidyl ester, the dyes absorb and emit between 770 and 810 nm. The quantum yield is in the range of about 25% to 35%, depending upon the solvent.

Another preferred compound within this embodiment is the compound wherein X is NCS, each of $R_2$ and $R_5$ is OMe and each of $R_3$ and $R_4$ is $(CH_2)_pSO_3^-$, where p is an integer from 2–4.

A further set of preferred compounds within the first embodiment above are those in which X is not a reactive group, i.e., wherein X is H, $NO_2$, OMe or $(CH_2)_wCH_3$, and wherein one of $R_3$ or $R_4$ is $(CH_2)_m$OH, $(CH_2)_m$phosphoramidite, $(CH_2)_m$NH_2, $(CH_2)_m$NCS, $(CH_2)_m$ COOH or $(CH_2)_m$COONHS-ester or $((CH_2)_m$COON-hydroxy sulfosuccinimidyl ester and the other of $R_3$ or $R_4$ is $(CH_2)_rCH_3$ or $(CH_2)_pSO_3^-$, wherein w is an integer from 0 to 19, m is an integer from 1 to 20, r is an integer from 0 to 19 and p is an integer from 2 to 4. Preferably, each of w and r, independently, is 0–6, and, most preferably, 1–3, and m is 1–6, most preferably 3–6. In a most preferred selection, X is H, one of $R_3$ and $R_4$ is $(CH_2)_m$OH, $(CH_2)_m$phosphoramidite, $(CH_2)_m$NH_2, $(CH_2)$NCS, $(CH_2)_m$COOH, $(CH_2)_m$COONHS-ester or $(CH_2)_m$COON-hydroxy sulfosuccinimidyl ester and the other of $R_3$ or $R_4$ is $(CH_2)_pSO_3$, each of $R_2$ and $R_5$ is either H or $SO_3^-$, and m is 1 to 6 and p is 2 to 4.

One set of preferred compounds within the second embodiment above includes compounds wherein X is NCS, $(CH_2)_n$OH, $(CH_2)_n$phosphoramidite, $(CH_2)_n$NH_2, $(CH_2)_n$ NCS, $(CH_2)_n$COOH, $(CH_2)_n$COONHS-ester, or $(CH_2)_n$ COON-hydroxy sulfosuccinimidyl ester; and $R_3$ and $R_4$ are independently selected from $(CH_2)_rCH_3$ or $(CH_2)_pSO_3^-$. In this set of compounds, it is preferred that n is an integer from 1 to 3, p is an integer from 2 to 4, and r is an integer from 0 to 19, most preferably 0 to 6.

A second set of preferred compounds within this second embodiment includes compounds wherein X is H, $NO_2$, OMe or $(CH_2)_wCH_3$; one of $R_3$ or $R_4$ is $(CH_2)_m$OH, $(CH_2)_m$ phosphoramidite, $(CH_2)_m$NH_2, $(CH_2)_m$NCS, $(CH_2)_m$ COOH, $(CH_2)_m$COONHS-ester or $(CH_2)_m$COON-hydroxy sulfosuccinimidyl ester, and the other of $R_3$ and $R_4$ is either $(CH_2)_rCH_3$ or $(CH_2)_pSO_3^-$; wherein w is 0 to 19, m is 1 to 20, r is 0 to 19 and p is 2 to 4. Preferably, w is 0 to 6, m is 1 to 6, and r is 0 to 6, and, most preferably, each of w and r, independently, is 1 to 3 and m is 3 to 6. Especially preferred compounds within this class include those where X is H or OMe, $R_5$ is H, one of $R_3$ or $R_4$ is $(CH_2)_m$NCS and the other is $(CH_2)_pSO_3^-$. In each of these compounds, the dye has an isothiocyanate group (NCS) as a reactive group for attachment of a biomolecule. In this embodiment, when X is H, the maximum absorption wavelength is 787 nm in methanol and 801 nm in DMSO, and the maximum emission wavelength is 807 nm in methanol and 818 nm in DMSO. When X is —$OCH_3$, the maximum absorption wavelength is 786 nm in methanol and the maximum emission wavelength is 806 nm in methanol. In both cases, the quantum yield is greater than 15%.

Other preferred compounds are those wherein X is H, one of $R_3$ or $R_4$ is $(CH_2)_pSO_3^-$ and the other is $(CH_2)_m$OH, $(CH_2)_m$-phosphoramidite, $(CH_2)_m$COOH, $(CH_2)_m$ COONHS-ester, $(CH_2)_m$COON-hydroxy sulfosuccinimidyl ester, or $(CH_2)_m$NH_2. Especially preferred are those compounds wherein one of $R_3$ and $R_4$ is $(CH_2)_{3-4}SO_3^-$ and the other is $(CH_2)_mOH$ or its phosphoramidite, 6-carboxypentyl or its NHS ester derivative, 3-aminopropyl or 3-isothiocyanatopropyl and $R_5$ is H or $SO_3^-$. When one of $R_3$ or $R_4$ contains a reactive hydroxy group, that hydroxy group can be converted to an N-hydroxy succinimidyl carbonate to permit coupling of the dye to biological molecules, such as to DNA strands, for sequencing purposes. It also can be directly phosphitylated for use as a dye-labeled phosphoramidite in DNA synthesis.

Within the third embodiment of the general formula, one set of preferred compounds comprises those in which X is NCS, $(CH_2)_nOH$, $(CH_2)_nNCS$, $(CH_2)_nCOOH$, $(CH_2)_nCOONHS$-ester or $(CH_2)_nCOON$-hydroxy sulfosuccinimidyl ester, and $R_3$ and $R_4$ independently are selected from $(CH_2)_rCH_3$ and $(CH_2)_pSO_3^-$. Preferably, n is an integer from 1 to 3 and r is an integer from 1 to 6, most preferably 3 to 6. A second set of preferred compounds includes compounds wherein X is not a reactive group but is selected from H, OMe, $NO_2$, or $(CH_2)_wCH_3$, one of $R_3$ and $R_4$ is $(CH_2)_mCH_3$ or $(CH_2)_pSO_3^-$ and the other is selected from $(CH_2)_mNH_2$, $(CH_2)_mNCS$, $(CH_2)_mCOOH$ or $(CH_2)_mCOONHSE$ or $((CH_2)_mCOON$-hydroxysulfosuccinimidyl ester. Preferably, each of r and w, independently, is 0 to 6 and m is 1 to 6. In a most preferred set of compounds, X is H and one of $R_3$ or $R_4$ is carboxypentyl or its NHS-ester, 6-hydroxyhexyl or its phosphoramidite, 3-aminopropyl, or 3-isothiocyanatopropyl and the other of $R_3$ and $R_4$ is $(CH_2)_pSO_3^-$.

As noted above, any of these compounds can be used to label a biological molecule to provide a labeled product that absorbs in the far red, near infrared or infrared regions. Biological molecules which can be labeled include, but are not limited to, natural and synthetic DNA, RNA, PNA, peptides, proteins, antibodies, antigens, polysaccharides, oligosaccharides, nucleosides, nucleotides and analogs thereof. The preferred biological molecules are DNA and RNA, oligonucleotides, nucleosides, nucleotides and analogs thereof.

The compounds of this invention can be attached, for example, to analogs of nucleotide triphosphates (dNTPs and ddNTPs) to provide a reagent for enzymatic labeling of various DNA molecules and for facilitating their detection with an automated DNA sequencing and analysis system. See, Narayanan, N., et al., Near-Infrared Dyes for High Technology Applications, S. Daehne et al. (eds.) 1998, Kluwer Academic Publishers (1998), pp. 141–158, incorporated herein by reference. DNA sequencing reaction products can be labeled internally by performing limited polymerization utilizing the labeled dNTP as the sole source of a particular deoxynucleotide prior to a dideoxy-specific termination reaction. PCR products also can be labeled fluorescently by the addition of limited quantities of the labeled dNTP to the amplification reaction. Such labeling can be useful, for example, for the detection of short tandem repeat polymorphisms (STRPs), which in turn are useful for gene mapping, genetic diagnostics, forensic analyses and paternity testing.

Examples of nucleotide analogs and DNA chain terminators that can be labeled with the dyes of this invention include those listed, for example, in U.S. Pat. Nos. 5,332,666; 5,151,507; 5,047,519; 5,091,519; 4,711,955 and 5,241,060 and PCT Application publication WO 9504747.

The synthesis of the cyanine dyes as encompassed and described by the general formula above is useful as it provides three different groups of dyes, each of which induces a wide range of wavelength choices suitable for excitation by commercially available lasers.

The presence of a nucleophile, such as an OH group, on the cyanine dye enables the dye to form an adduct with a biological molecule. For example, an OH group can be activated by disuccinimidylcarbonate (DSC) to an N-hydroxy succinimidyl carbonate (NHSC) that will react with a nucleophile such as OH to form a carbonate ester or with a primary amine to form a carbamate linkage. Alternatively, the OH group on the dye can be activated by a phosphitylating reagent, such as N,N-diisopropyl amino-2-cyanoethyl chlorophosphine or 2-cyanoethyl-bis-(N,N-disopropylamino)phosphoramidite), to form a phosphoramidite intermediate. These phosphoramidites are capable of reacting with another hydroxy group on the target biomolecule to provide a dye conjugate and are particularly suitable for synthesizing a dye labeled oligonucleotide.

Alternatively, if the dye compound comprises an amino group, the amino group can be derivatized to various analogs. For example, a primary amine reacts with a carboxylic acid containing biomolecule, resulting in a stable peptide linkage. A primary amino group also can be derivatized with an iodoacetic or bromoacetic acid or N-ε-maleimidocaproic acid to form a linker that will be reactive towards a sulfhydryl (SH) group on the biomolecule. Further, the primary amine can be reacted with thiophosgene to make an isothiocyanate reactive functionality. The primary amines also can be reacted with carboxaldehyde groups resulting in Schiff's base products.

The presence of an isothiocyanate group (NCS) on the heptamethine cyanine dye enables an efficient labeling of biomolecules such as proteins, antibodies, oligonucleotides, nucleotides, and analogs thereof containing a primary amine group, resulting in a stable thiourea linkage. A carboxylic acid functional group can form a stable peptide linkage with a primary amine group or an ester linkage with an alcohol when reacted in the presence of a catalyst. Alternatively, the carboxylic acid can be used in its activated form, N-hydroxysuccinimidyl ester (NHS-ester or NHSE); NHSE is especially stable during long-term storage and easy to handle.

The presence of a sulfonic acid group within a dye molecule confers an advantage of enhanced water solubility. Additionally, sulfonic acid groups also are advantageous as they provide increased photostability, brightness and considerable reduction of interaction with surrounding molecules. The enhanced water solubility provided by sulfonic acid groups is highly desirable. Biological molecules, such as DNA, RNA, proteins and antibodies are intrinsically water soluble. The hydrophilic nature of these molecules enable them to carry out their respective biological functions inside cells. In contrast, unmodified fluorescent dyes are generally hydrophobic in nature. In order to label a biological molecule with a fluorescent dye, it is desirable to synthesize an organic fluorescent dye that is soluble in water as the use of some organic solvents can affect the activity of the biomolecule. The enhanced water solubility often is achieved by using dyes which contain one or more sulfonic acid groups. In the first embodiment of the general formula above, for example, the compound where both $R_2$ and $R_5$ are $SO_3^-$ and $R_3$ and $R_4$ are sulfonatobutyl shows excellent water solubility because of its four sulfonic acid groups, and the compound is highly desirable for labeling antibodies and proteins.

Those dyes within the scope of this invention which do not contain at least one sulfonic acid group and are not, or are only slightly, water soluble still can be important in labeling biomolecules provided the organic solvent or cosolvent selected is one which no more than minimally affects the activity of the biomolecule. Such solvents can include, for example, DMF and DMSO.

In addition to increased water solubility, the presence of one or more sulfonate groups on the fluorescent dye molecule confers an overall net negative charge to the molecule. This net negative charge helps minimize non-specific hydrophobic interaction with biomolecules. It also helps minimize nonspecific background caused by free dye (unbound to the biomolecule) seen on gel electrophoretic sequencing in which they move in the opposite direction to that of the DNA strands.

In accordance with one aspect of the present invention, two infrared dyes from those discussed above can be selected wherein each has its excitation and/or emission spectra spaced sufficiently from the other that the fluorescence from each dye can be distinguished from the other dye either by the wavelength that excites it into fluorescence, or the wavelength at which it fluoresces or both, or by the fluorescence lifetime of the dye. The wavelength spacing is maintained sufficiently close to be excited by laser diodes. The dyes can be incorporated in probes and primers for attachment to oligonucleotides by such methods as described, for example, in Ruth, Jerry L. (1984) DNA 3, 123. The dyes can be newly synthesized or prepared by modifying existing, commercially available dyes.

There are many dyes suitable for such modification, such as, for example: (1) 3,3'-diethylthiadicarbocyanine iodide; (2) 3,3'-diethylthiatricarbocyanine perchlorate; (3) 3,3' diethyloxatricarbocyanine iodide; 1,1',3,3,3'-hexamethylindotricarbocyanine perchlorate; (5) 1,1'-diethyl-2,2'-dicarbocyanine iodide; (6) 3,3' diethylthiadicarbocyanine iodide; (7) 3,3'-diethyloxatricarbocyanine iodide; (8) 1,1',3,3,3',3'-hexamethylindotricarbocyanine perchlorate; (9) 1,1',3,3,3',3'-hexamethylindotricarbocyanine iodide; and (10) indocyanine green.

In the uncatalyzed synthesis of new heptamethine cyanine dyes which are potential precursors for making functionalized near-infrared labels, a mixture of a quaternary salt of a heterocyclic base containing an activated methyl group (2 equiv) and 2-chloro-1-formyl-3-(hydroxymethylene) cyclohex-1-ene, an unsaturated bisaldehyde derived from cyclohexanone (1 equiv) is heated to reflux in a mixture of 1 butanol and benzene (7:3) as solvent, without using any catalyst. The water formed during the reaction is removed as an azeotrope by a Dean-Stark condenser. The reactions generally require 3–12 h for completion. The resulting product is generally pure after simple filtration of the dye from the crude reaction mixture followed by washings with diethyl ether. A wide range of 2-methy-1-alkyl quaternary salts of various indole and benzindole and analogous sulfur and oxygen heterocyclic derivatives undergo this reaction in a facile manner to form the corresponding symmetric dyes. An important feature of the current method is that the slower rate of the reaction allows one to prepare nonsymmetric dyes derived from two different heterocycles in a single pot in a fairly good yield. The syntheses of these nonsymmetric dyes become important when changes in the spectral and physical properties of the dyes are desired for specific application and compatibility with the instrumentation. These changes can be incorporated by appropriately modifying the structural design of the dyes.

Dye synthesis is illustrated by charts 1–3, below. In the charts, Z, X, $X_1^{\pm}$, and each of $R_1$–$R_6$ are as defined in Formula I. $X_2^{\pm}$ is selected from the same group as $X_1^{\pm}$.

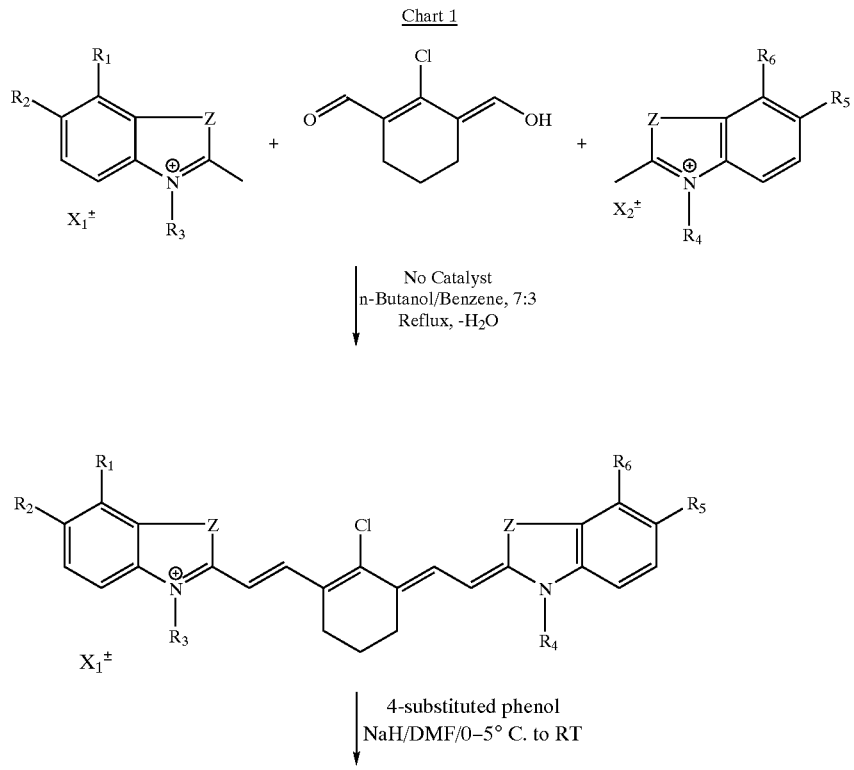

Chart 1

-continued
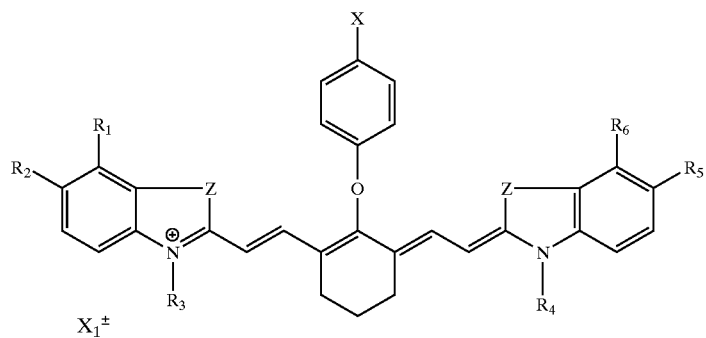
Chart 2
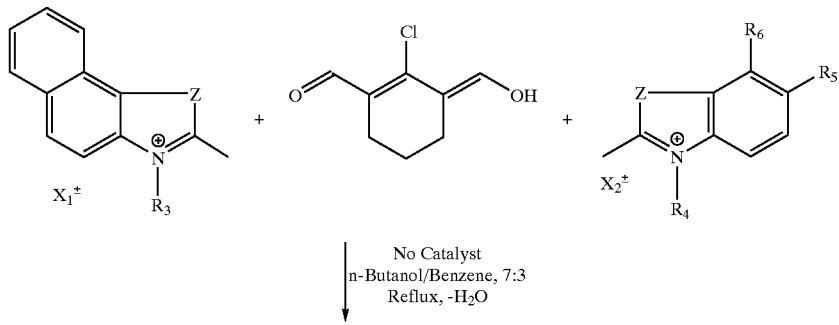
↓ No Catalyst
n-Butanol/Benzene, 7:3
Reflux, -H₂O
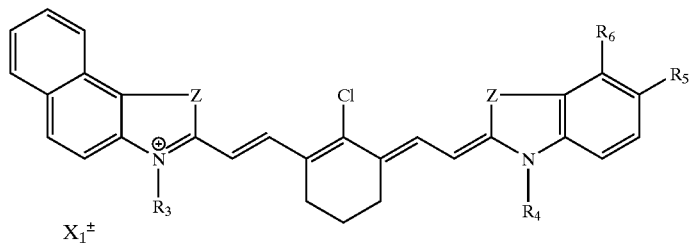
↓ 4-substituted phenol
NaH/DMF/0–5° C. to RT
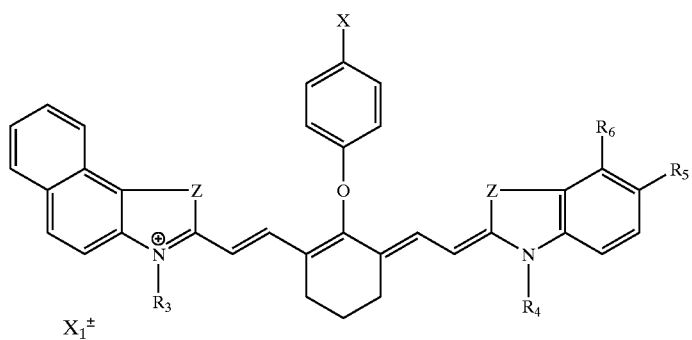

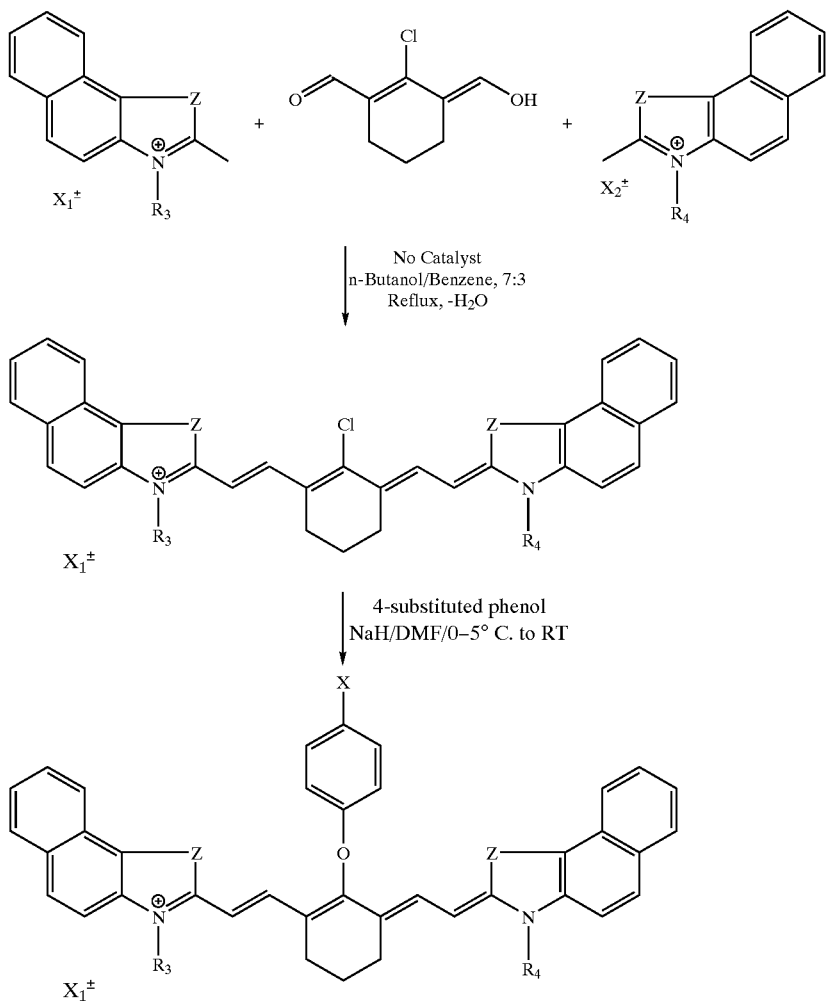

Chart 3

Depending upon the identity of Z, chart 1 shows the synthesis of dyes from indoles, benzothiazoles and/or benzoxazoles and analogs thereof; chart 2 shows the synthesis of dyes from an indole, benzothiazole or benzoxazole and a benzindole, naphthiazole or naphthaxazole and analogs thereof; and chart 3 shows the synthesis of dyes from benzindoles, naphthiazoles and/or naphthoxazoles and analogs thereof.

In a specific illustration, the foregoing general method can be used to synthesize a NHS ester-containing compound as illustrated in Example 1 below.

As noted above, the compounds of this invention are useful for labeling and sequencing DNA and RNA sequences.

FIG. 1 shows a perspective view of an embodiment of sequencer in which sequencing using compounds of this invention can be performed. This sequencer is described in structure and operation in the aforementioned U.S. patent application Ser. No. 07/570,503 filed Aug. 21, 1990; U.S. patent application Ser. No. 07/078,279 filed Jul. 27, 1987; and U.S. Pat. No. 4,729,947, all of which are entitled DNA SEQUENCING and which were filed by Middendorf et al.

Figure 2:
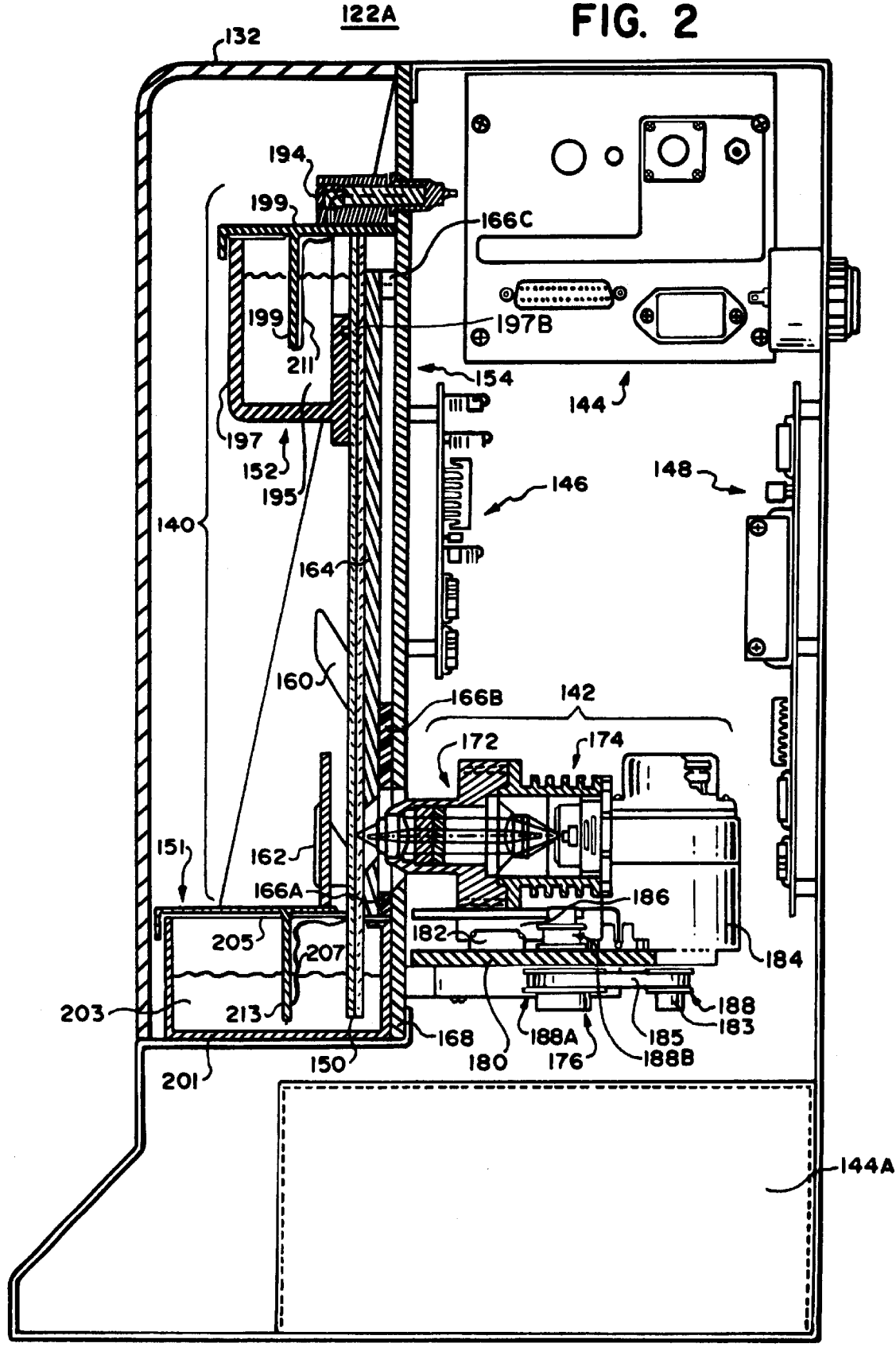
FIG. 2 is a sectional view taken through lines 2—2 of FIG. 1.

In FIG. 2, there is shown a sectional view of the remote station 122A taken through section lines 2—2 of FIG. 1 having an electrophoresis section 140, a scanning section 142, an electrophoresis power supply 144, a system power supply section 144A, an analog board 146 and a digital board 148. The electrophoresis section 140 is positioned near the front of the cabinet and a portion of it is adapted to be scanned by the scanning section 142 in cooperation with circuitry on the analog board 146 and the digital board 148. All of the apparatus are electrically connected to the power supply section 144A for such operation.

To separate different DNA fragments into bands, the electrophoresis section 140 includes a gel sandwich 150, an upper buffer assembly 152, support assembly 154, and a lower buffer assembly 151 positioned to enclose the bottom of the gel sandwich 150. In the embodiment of FIG. 2, the gel sandwich 150 is held vertically and its temperature is controlled during operation. Bands are separated by applying voltage to the upper buffer assembly 152 and lower buffer assembly 151 and scanned by the scanning section 142.

To support the gel sandwich 150, the support assembly 154 includes a pair of upper side brackets and lower side brackets 160 and 162 (only one of each pair being shown in FIG. 2), an apparatus support plate 168, a temperature control heating plate 164, and a plastic spacer, shown at 166A–166C, in FIG. 2. The entire structure is supported on the apparatus support plate 168 which mounts the upper and lower side brackets 160 and 162.

The upper and lower side brackets 160 and 162 are each shaped to receive a pin (not shown) extending from one or the other side of the gel sandwich 150 and hold it in place in juxtaposition with the scanning section 142. The spacers as shown as 166A–166C space the temperature control heating plate 164 from the apparatus support plate 168 and maintain it at a constant selected temperature above ambient temperature. In the preferred embodiment, the temperature is maintained at 45–50 degrees Centigrade and should be maintained in a range of 30 degrees to 80 degrees.

The scanning section 142 includes a laser diode assembly (not shown in FIG. 2), a microscope assembly 172, a photodiode section 174 and a scanner mounting section 176. The laser diode assembly (not shown in FIG. 2) is positioned at an angle to an opening in the heating plate 164 so that light impinges on the gel sandwich 150 to cause fluorescence with minimum reflection back through the microscope assembly 172.

To receive the fluorescent light, the microscope assembly 172 is focused on the gel sandwich 150 and transmits fluorescent light emitted therefrom into the photodiode section 174 which converts it to electrical signals for transmission to and processing by the analog and digital boards 146 and 148 which may provide further analysis of data. The scanning section 142 moves along a slot in the apparatus support plate 168 which is mounted to the scanner mounting section 176 during this operation in order to scan across the columns in the gel sandwich 150.

The scanner mounting section 176 includes a mounting plate 180, a bearing plate 182, a stepping motor 184, a slidable support 186 and a belt and pulley arrangement 185, 188A and 188B. The mounting plate 180 is movably mounted to the apparatus support plate 168 through a frame member and supports the elongated bearing plate 182, the stepping motor 184 and two pulleys 188A and 188B. The elongated bearing plate 182 extends the length of the gel sandwich 150.

To permit motion of the laser diode assembly (not shown) and microscope assembly 172 with respect to the gel sandwich 150, the slidable support 186 supports the microscope assembly 172 and diode assembly and slidably rests upon the bearing plate 182. An output shaft 183 of the stepping motor 184 drives a pulley 188B through pulley 188, belt 185, and pulley 188A and the pulley 188B drives a belt (not shown) that is clamped to the slidable support 186 to move it the length of the gel sandwich 150 during scanning by the laser diode and microscope assembly 172 which rest upon it. The stepping motor 184 under the control of circuitry in the digital board 148 moves the pulley 188B to move the belt (not shown) and thus cause scanning across the gel sandwich 150.

As shown in this view, the electrophoresis power supply 144 is electrically connected to buffer in the upper buffer assembly 152 through an electrical connector 194 and to the lower buffer assembly 151 through a connector not shown in FIG. 2.

The upper buffer assembly 152 includes walls 197 forming a container to hold a buffer solution 195 and a cover 199 formed with a lip to fit over the walls 197 from the top and containing a downwardly extending flat member spaced away from the side walls and holding a conductor 211.

The conductor 211 is electrically connected to the source of power through connector 194 which is mounted to the top of the cover 199 to permit electrical energization of the buffer solution 195.

The bottom buffer assembly 151 includes enclosed walls 201 defining a container for holding a buffer solution 203 and a cover 205 closing the container 201 and having a downwardly extending portion 213 extending into the buffer 203 for supporting a conductor 207 for applying energy to the bottom buffer solution 203. The gel sandwich 150 extends downwardly into the buffer solution 203 and upwardly into the buffer solution 195 to permit the electrical contact for electrophoresis. An "o" ring 197B provides a seal for the upper buffer assembly 152 so that the buffer solution 195 does not empty out of the upper buffer assembly 152.

Figure 3:
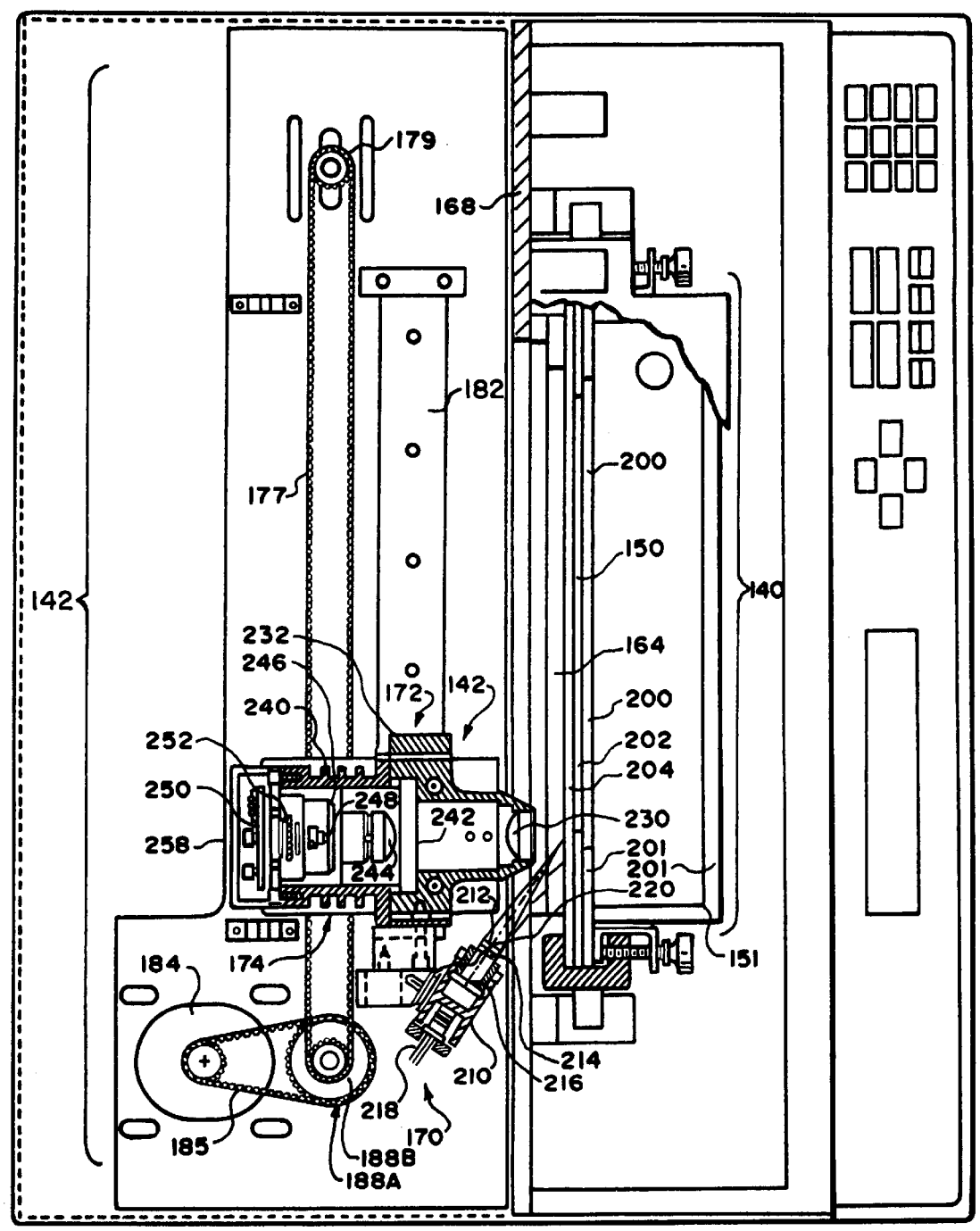
FIG. 3 is a sectional view of a portion of FIG. 1 taken through lines 3—3.

In FIG. 3, there is shown a sectional view taken through lines 3—3 of FIG. 1 showing a portion of the electrophoresis section 140, a portion of the scanning section 142 (indicated twice in FIG. 3 for clarity) and the electrophoresis power supply section 144 (FIG. 2 only) mounted together to illustrate, from a top view, the arrangement of the apparatus support plate 168, the heater plate 164, the gel sandwich 150, a laser diode assembly 170, a microscope assembly 172 and a photodiode assembly 174. The heater plate 164 and apparatus support plate 168 have slots running in a horizontal direction orthogonal to the lanes of DNA in the electrophoresis section 140 sized to receive the ends of the laser diode assembly 170 and the microscope section 172 for scanning thereof.

To cooperate with the separation and scanning of DNA bands, the gel sandwich 150 includes a front glass plate 200, a gel section 202 and a rear glass plate 204 mounted in contact with the heater plate 164 and having a section exposed for scanning by the laser diode assembly 170 and the microscope assembly 172. The rear glass plate 204 contacts the heater plate 164 and is separated from the front glass plate 200 by the gel section 202 within which DNA separation takes place. The front and rear glass plates 200 and 204 may be any type of glass but are preferably soda lime which has low fluorescence in the far red and near infrared regions and is prepared by a process that provides optically flat surfaces without grinding.

To transmit light to the gel sandwich 150, the laser diode assembly 170 includes a housing 210 a focusing lens 212, a narrow band pass filter 214, a collimating lens 216 and a laser diode 218. The laser diode 218 emits far red, near infrared, or infrared light which is collimated by the laser collimating lens 216 and filtered through the narrow band pass filter 214. This light is focused by the focusing lens 212 onto the gel sandwich 150. Preferably, the point of focus on the gel section 202 of the gel sandwich 150 lies along or near the central longitudinal axis of the microscope section 172 and the photodiode section 174.

The thickness of the glass plates and the gel, the position of the laser and microscope assembly 172 and thus the angle of incidence and angle of reflection of the light from the laser and to the microscope assembly 172 are chosen, taking into consideration the refractive index of the gel and glass and the thickness of the glass plates and the gel, so that the light from the laser is maximally transmitted to the gel. The light from the laser is not directly reflected back because the angle of incidence to normal is equal to the Brewster's angle at the first interface and is such as to impinge on the markers with full intensity after refraction but not be reflected by the first surface of the gel sandwich 150 into the microscope assembly 172 and the microscope assembly 172 views those markers that fluoresce in its line of sight.

To maintain temperature control over the laser diode, the housing 210: (a) is coupled to a heat sink through a thermal electric cooler 220, and (b) encloses the focusing lens 212, narrow band pass filter 214, collimating lens 216 and laser diode 218; and (c) accommodates the electrical leads for the diode.

To receive and focus light emitted by fluorescent markers from the gel section 202 in response to the light from the laser diode assembly 170, the microscope assembly 172 includes a collection lens 230, a housing 232 and a focusing motor. The microscope assembly 172 is adapted to be positioned with its longitudinal axis centered on the collection lens 230 and aligned with the photodiode section 174 to which it is connected. For this purpose, the housing 232 includes a central passageway in which are located one or more optical filters (not shown) with a pass band matching the emission fluorescence of the marked DNA strands. With this arrangement, the collection lens 230 receives light from the fluorescent material within the gel section 202 and collimates the collected light for optical filtering and then transmission to the photodiode assembly 174.

To generate electrical signals representing the detected fluorescence, the photodiode assembly 174 includes a housing 240 having within it, as the principal elements of the light sensors, an inlet window 242, a focusing lens 244, a sapphire window 246 and an avalanche photodiode 248. To support the avalanche photodiode 248, a detector mounting plate 250 is mounted within the housing 240 to support a plate upon which the avalanche photodiode 248 is mounted. The inlet window 242 fits within the housing 240 to receive light along the longitudinal axis of the photodiode assembly 174 from the microscope assembly 172.

Within the housing 240 of the photodiode assembly 174, the sapphire window 246 and avalanche photodiode 248 are aligned along the common axis of the microscope assembly 172 and the photodiode assembly 174. The focusing lens 244 focuses light transmitted by the microscope assembly 172 onto a small spot on the avalanche photodiode 248 for conversion to electrical signals. A thermoelectric cooler 252 utilizing the Peltier effect is mounted adjacent to the detector mounting plate 250 to maintain a relatively cool temperature suitable for proper operation of the avalanche photodiode 248.

As best shown in this view, the stepping motor 184 rotates the belt 185 to turn the pulley 188A, which, in turn, rotates pulley 188B. The pulley 188B includes a belt 177 extending between it and an idler pulley 179 51 and attached at one location to the slidable support 186 (shown only in FIG. 2) to move the scanning microscope and laser lengthwise along the gel sandwich 150 for scanning purposes. The motor 184, by moving the carriage back and forth, accomplishes scanning of the gel sandwich 150.

Figure 4:
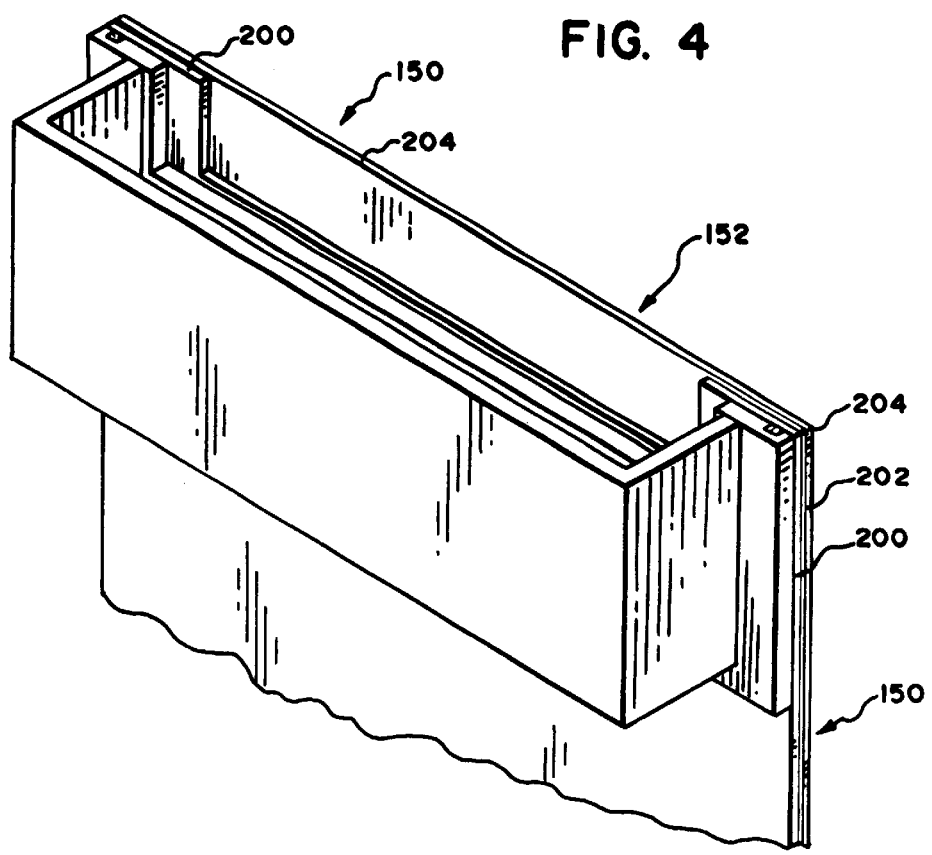
FIG. 4 is an exploded perspective view of a portion of the embodiment of FIG. 2.

In FIG. 4, there is shown a fragmentary perspective view of the gel sandwich 150 and the upper buffer assembly 152 mounted to each other showing the outer glass plate 200 cut away from the rear glass plate 204 to expose the gel section 202 to buffer solution within the upper buffer assembly 152. With this arrangement, DNA samples may be pipetted between the glass plates 200 and 204 and moved downwardly by electrophoresis beyond the upper buffer assembly 152 and through the gel sandwich 150 to the bottom buffer (not shown in FIG. 4).

Figure 5:
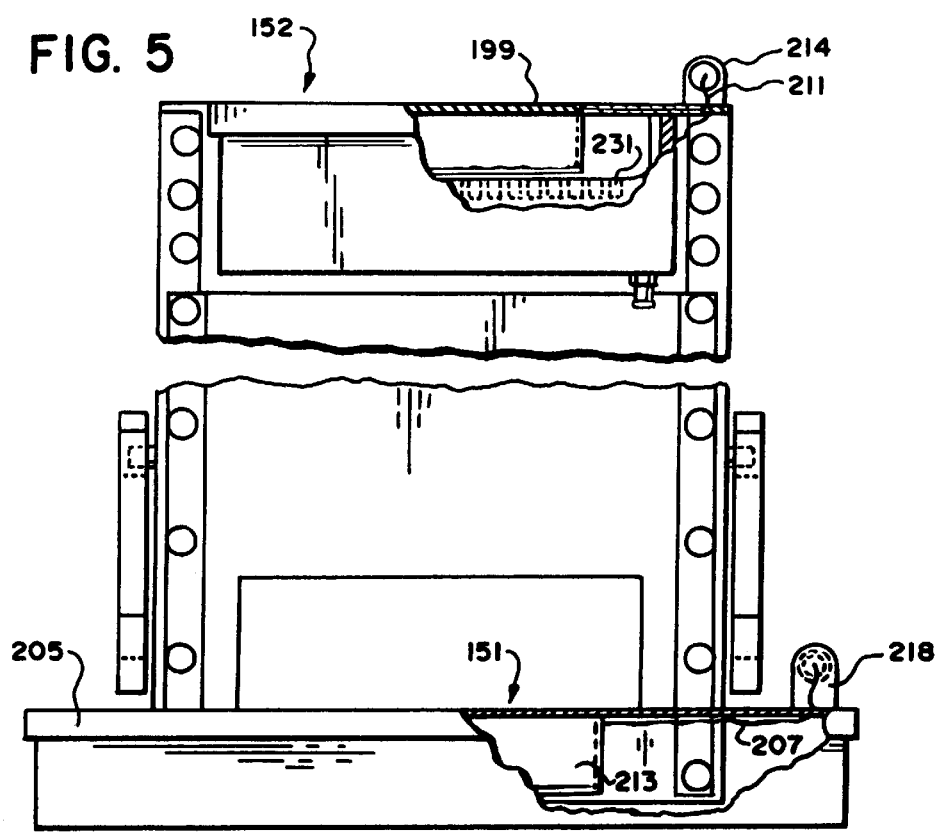
FIG. 5 is an enlarged view, partly broken away, of a portion of the embodiment of FIG. 2.

In FIG. 5, there is shown a broken away view of the gel sandwich 150 illustrating the upper buffer assembly 152 and the lower buffer assembly 151 connected to it at each end. As shown in this view, the cover 199 includes a connecting post 214 which receives the conductor 211 for connection to the downwardly extending portion of the cover 199 into the buffer compartment. Between the glass plates 200 and 204 (FIG. 4) of the gel sandwich 150, are a plurality of downwardly extending recesses 231 in the gel section 202 (FIG. 4) between the plates. A DNA sample is pipetted into these recesses to form channels for electrophoresing to the lower buffer assembly 151.

To form an electrical connection through the gel sandwich 150 from the upper buffer assembly 152 to the lower buffer assembly 151, a connecting post 218 is connected to the cover 205 of the lower buffer assembly 151 for receiving the conductor 207 which extends downwardly to the downwardly extended plate 213 and into the buffer solution.

Figure 6:
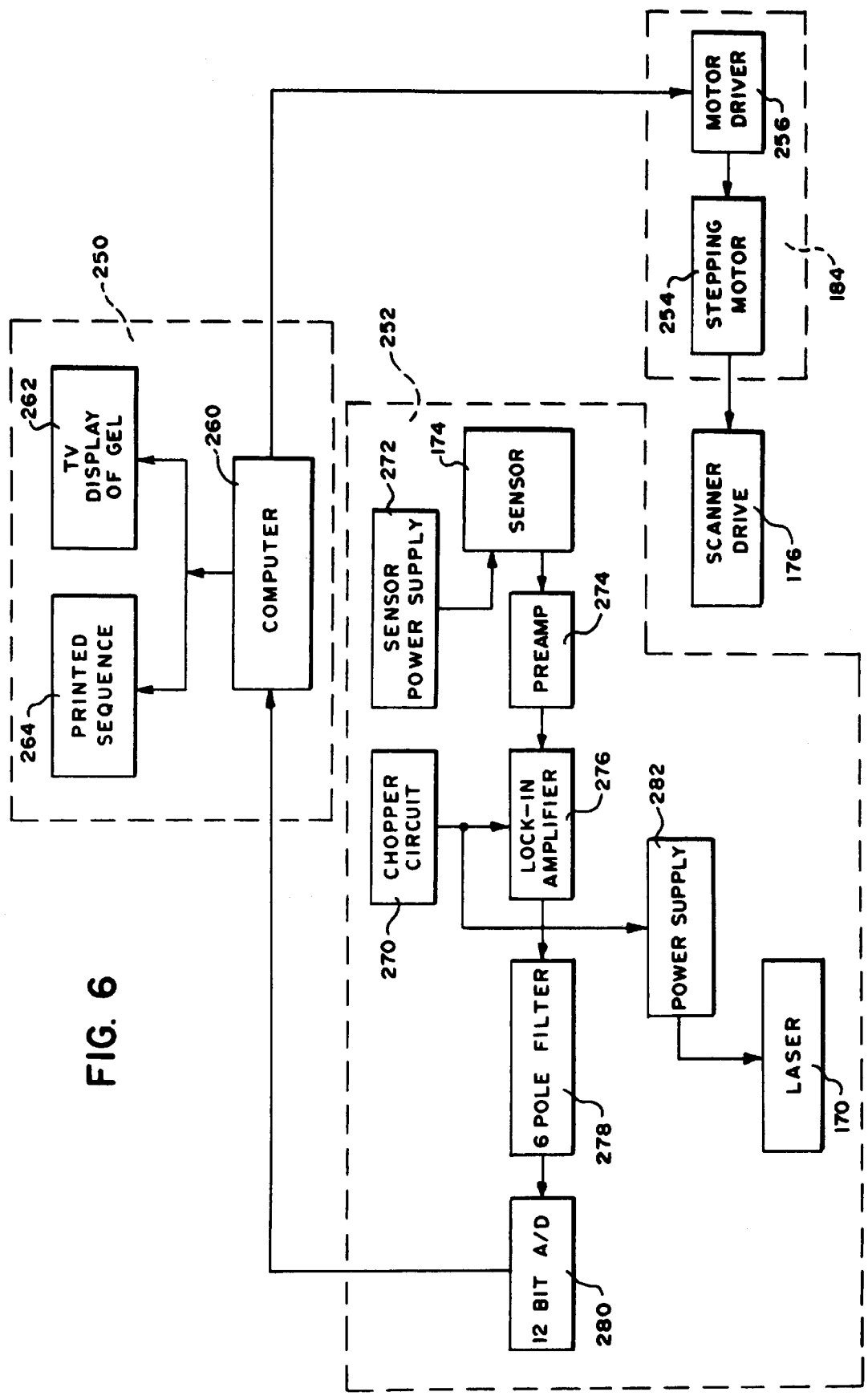
FIG. 6 is a block diagram of a circuit that may be used for coordination of a sensor, scanner drive, and laser used.

In FIG. 6, there is shown a block diagram of the circuitry used to control the remote station 122A of the embodiment of FIG. 2 having a control, correlation and readout section 250, the scanner drive 176, the motor assembly 184 for moving the scanner drive 176, and the sensing configuration 252. The sensing configuration 252 includes the laser assembly 170 and the sensor assembly 174 which receives signals, removes some noise, and transmits the signals for display and readout in the control, correlation and readout section 250, while the scanner drive 176 and motor for the scanner drive 184 receive signals from the control, correlation and readout section 250 to control the motion of the sensor back and forth across the gel sandwich. This overall configuration is not part of the invention of this application except insofar as it cooperates with the sensing configuration 252 to scan the DNA and determine its sequence in accordance with the embodiments of FIGSs. 1–5.

To drive the sensor 174 from position to position, the motor assembly 184 includes a stepper motor 254 and a motor driver 256. The motor driver 256 receives signals from the control correlation and readout section 250 and actuates the stepper motor 254 to drive the scanner drive 176. The scanner drive 176 is mechanically coupled to a stepping motor 254 through a belt and pulley arrangement for movement back and forth to sense the electrophoresis channels on the gel sandwich 150 (FIG. 3). The stepping motor 254 and driver circuitry 256 are conventional and not themselves part of the invention.

The control, correlation and readout system 250 includes a computer which may be any standard microprocessor 260, a television display or cathode ray tube display 262 and a printer 264 for displaying and printing the results of the scans.

To sense data, the sensing configuration 252 includes, in addition to the laser 170 and the sensor 174, a chopper circuit 270, a sensor power supply 272, a preamplifier 274, a lock-in amplifier 276, a 6-pole filter 278, a 12-bit analogue to digital converter interface circuit 280 and a laser power supply 282.

The sensor 174 receives light from the laser 170 after it impinges upon the gel sandwich 150 (FIG. 3) and transmits the signals through preamplifier 274 to the lock-in amplifier 276. The sensor receives signals from the sensor power supply 272. The chopper circuit 270 provides pulses at synchronized frequencies to the lock in amplifier 276.

The laser 170 receives power from the power supply 282 which is controlled by the chopper circuit 270 so that the signal from the laser is in synchronism with the signal applied to the lock-in amplifier 276 so that the output from the lock-in amplifier 276 to the 6-pole filter 278 discriminates against unwanted signal frequencies. This signal is converted to a digital signal in the 12-bit analogue to digital converter 280 which serves as an interface to the computer 260.

With this arrangement, the scanning rate may be set to discriminate against noise and the synchronized demodulation from the chopper control further reduces noise, particularly discriminating against the natural fluorescense of the glass in the gel sandwich 150 (FIGS. 2 and 3 ).

Figure 7:
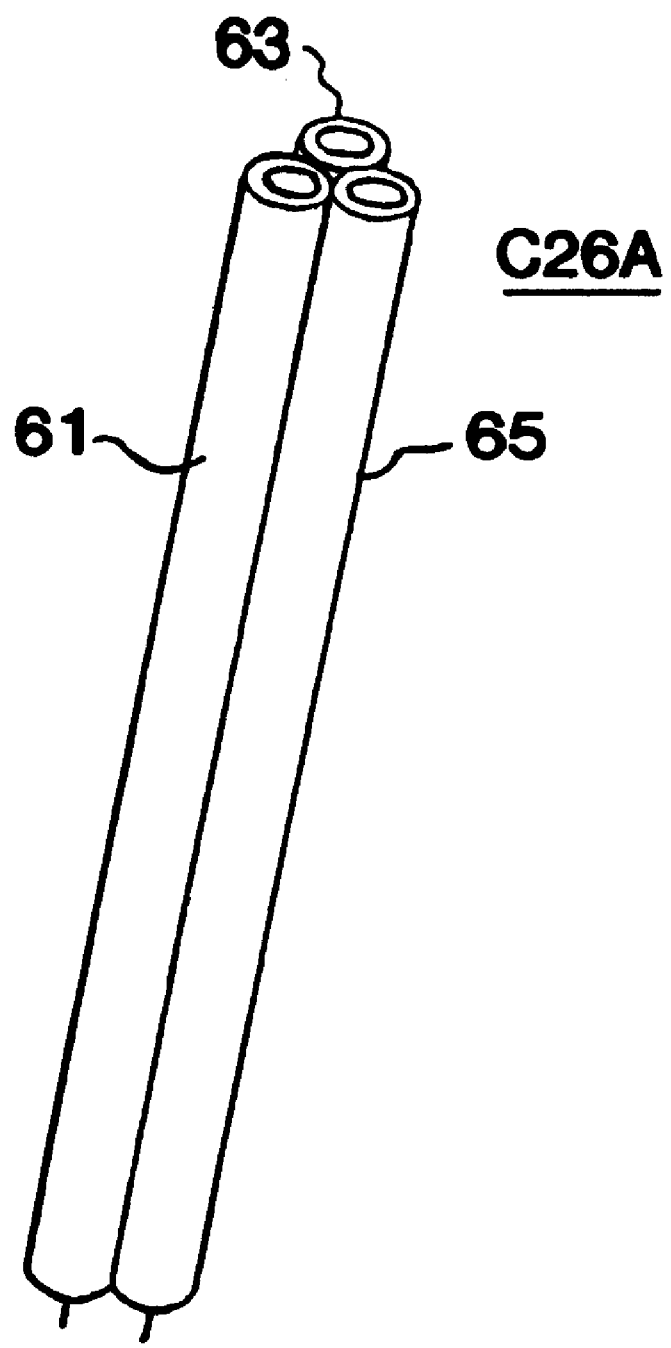
FIG. 7 is an embodiment of electrophoresis apparatus that may be used instead of the gel sandwich used in the embodiments of FIGS. 1–6.

In FIG. 7, there is shown another embodiment C26A which may be substituted for the gel sandwich 150 and includes capillary columns 61, 63 and 65 as commonly used in capillary electrophoresis. These columns may be filled with buffer solution or a gel and be used for electrophoresis. In such a case, several capillaries may be used as a substitute for the gel sandwich 150 of the embodiment of FIGS. 2–5. Thus, the same band of A, G, C or T type bases might flow through several parallel bundles of capillaries, or they might flow through only one capillary per type of base; or bands of A, G, C, and T type bases may be combined to flow through only one capillary.

The separation path such as gel channels or capillary tube length should be no longer than two meters for a range of lengths of DNA from 50 to 10,000 or more bases. However, as the range of DNA lengths increase, the time required increases. Also, the time required for each separation is in the range of from ½ second to 5 minutes for each added base of length separation.

From the above summary, it can be understood that the techniques for the sequencing of fluorescence labeled DNA of this invention have several advantages, such as: (1) because the dyes have their emission spectra in the far red, near infrared or infrared light spectrum, small inexpensive diode lasers may be used; and (2) this wavelength region is characterized by relatively low background fluorescence in glass, and, therefore, less noise in the received signal.

EXAMPLE 1

The following diagram illustrates the synthesis of an NHS-ester cyanine dye.

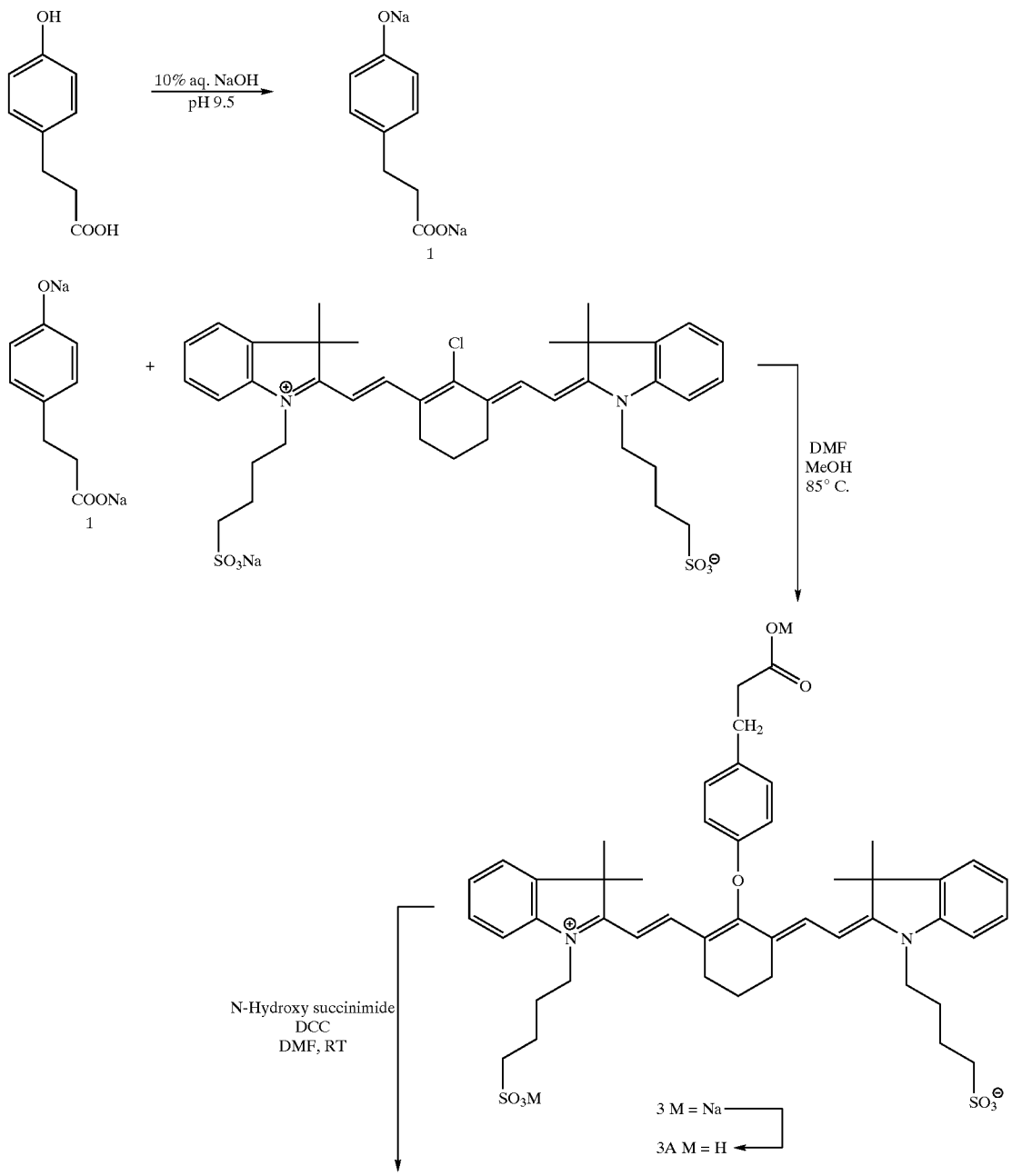

-continued

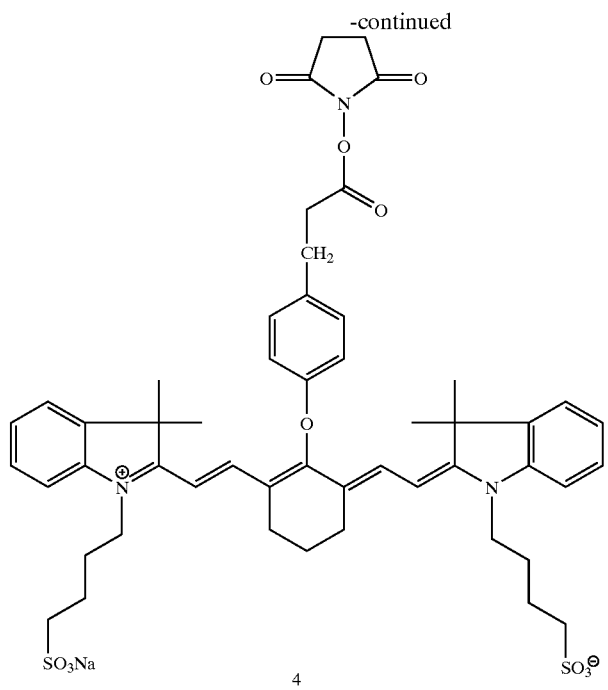

4

As shown in the above diagram, 4-hydroxyphenyl propionic acid (2 g.) was dissolved in water (25 ml.) and the resultant solution was titrated with a 10% NaOH solution to a pH of 9.5. The turbid solution was filtered through filter paper. The clear filtrate was precipitated in acetone (200 ml) with stirring. The precipitate was filtered and dried under vacuum to produce a powdery material of disodium salt 1.

The chloro dye 2 (670 mg., 0.92 mmol, MW 727) was dissolved in DMF (20 ml) under argon with stirring. Compound 1 (1.4 equivalent, 1.3 mmol., MW 208) was dissolved separately in a vial of methanol (7 ml.) until it all went into solution (about 30 minutes). The methanolic solution was added to the dye at room temperature. The reaction mixture was heated on an oil bath to 85° C. and the absorption maxima was checked and TLC and HPLC were run periodically (every 30–45 minutes).

To prepare the solution for TLC/HPLC, an aliquot of the reaction mixture (5 µl) was placed in an eppendorf tube and ether was added (200 µl). The contents of the tube were mixed well and centrifuged for 15 seconds. The light yellowish-green ether solution was decanted and the ether washing was repeated. The resultant green pellet was dissolved in methanol (10–20 µl) for TLC and UV-Vis or in water for HPLC. TLC was run on an RPC18 silica gel plate using 40% aqueous methanol.

The reaction to provide compound 3 was complete within 3 hours (the absorption maximum changed from 782 to 770). The reaction mixture was concentrated to dryness on the rotoevaporator. The residue was rinsed twice with 5% methanolic ether. The resultant gummy material was purified on RPC18 silica gel column using 40% aqueous methanol which was gradually increased to 30% and 20%. Fractions were collected and analyzed.

To convert the sodium salt 3 to the free acid 3A, 0.1 N sulfuric acid (5 ml) was added to the dry dye 3. The solution was concentrated and dried throughly.

To compound 3A were added an equal amount by weight of DCC and N-hydroxy succinimide. The resultant mixture was dissolved in dry DMF (5 ml) under argon and stirred at room temperature overnight. TLC and HPLC were monitored by the method described above. There was no change in the absorption maxima. After about 16 hours, the precipitate of urea was filtered through a dry sintered funnel followed by washings with dry DMF. The filtrate then was added to ether to precipitate the dye. The dye was filtered, washed with ether, dried for about 5 minutes and the resultant solid was transferred to a vial and dried further on the pump in a vacuum desiccator. the resulting powder material was ready for immediate use or could be stored cold.

The dye NHSE 4 was conjugated to an amine containing substrate. 1.5–2.0 equivalents of excess dye to the amine were used. The amine was dissolved in buffer (100 µl, either pH 8.5 borate buffer or pH 11.0 carbonate-bicarbonate, 50 mM) and DMF (200 µl). The dye was dissolved in water (100 µl) and added to the amine in aqueous solution with stirring. The reaction was monitored by HPLC. The reaction was completed in 2–3 hours. The reaction mixture was purified by prep. HPLC.

Although a preferred embodiment of the invention has been described with some particularity, many modifications and variations are possible within the light of the above description. Accordingly, within the scope of the appended claims, the invention may be practiced other than as specifically described.

What is claimed is:
1. A compound having the formula
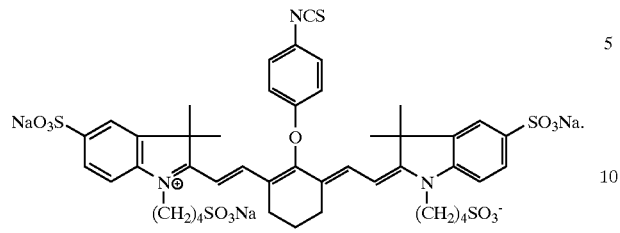
2. A biological molecule coupled to the compound of claim 1.
* * * * *